United States Patent [19]

Kapadia et al.

[11] Patent Number: 4,883,486

[45] Date of Patent: Nov. 28, 1989

[54] PROSTHETIC LIGAMENT

[76] Inventors: Indu Kapadia, 33 Front St., Denville, N.J. 07834; Kemal Schankereli, 7979 Neal Ave. N., Stillwater, Minn. 55082

[21] Appl. No.: 200,427

[22] Filed: May 31, 1988

[51] Int. Cl.$^4$ .............................................. A61F 2/08
[52] U.S. Cl. ................................. 623/13; 128/334 R
[58] Field of Search .............................. 623/13, 1, 66; 128/334 R, 335.5

[56] References Cited

U.S. PATENT DOCUMENTS

| | | | |
|---|---|---|---|
| 3,745,590 | 7/1973 | Stubstad | 623/13 |
| 3,973,277 | 8/1976 | Semple et al. | 623/13 |
| 3,987,497 | 10/1976 | Stoy et al. | 623/66 |
| 4,149,277 | 4/1979 | Bokros | 623/13 |
| 4,209,859 | 7/1980 | Hoffman | 623/13 |
| 4,301,551 | 11/1981 | Dore et al. | 623/13 |
| 4,345,339 | 8/1982 | Müller et al. | 623/13 |
| 4,455,690 | 6/1984 | Homsy | 623/13 |
| 4,483,023 | 11/1984 | Hoffman, Jr. et al. | 623/13 |
| 4,576,608 | 3/1986 | Homsy | 623/13 X |
| 4,584,722 | 4/1986 | Levy et al. | 623/13 |
| 4,585,458 | 4/1986 | Kurland | 623/13 |
| 4,642,119 | 2/1987 | Shah | 623/13 |
| 4,662,886 | 5/1987 | Moorse et al. | 623/13 |
| 4,668,233 | 5/1987 | Seedhom et al. | 623/13 |
| 4,713,075 | 12/1987 | Kurland | 623/13 |
| 4,728,329 | 3/1988 | Mansat | 623/13 |
| 4,790,850 | 12/1988 | Dunn et al. | 623/13 |

FOREIGN PATENT DOCUMENTS

| | | | |
|---|---|---|---|
| 1178441 | 9/1985 | U.S.S.R. | 623/13 |
| 8500511 | 2/1985 | World Int. Prop. O. | 623/13 |

*Primary Examiner*—Alan W. Cannon
*Attorney, Agent, or Firm*—Jacobson and Johnson

[57] ABSTRACT

A prosthetic ligament has an outer sheath of permeable PTFE yarn surrounding a core of synthetic filaments with stitching through the sheath and core holding the two firmly together to act as a single integral unit when placed in situ.

17 Claims, 2 Drawing Sheets

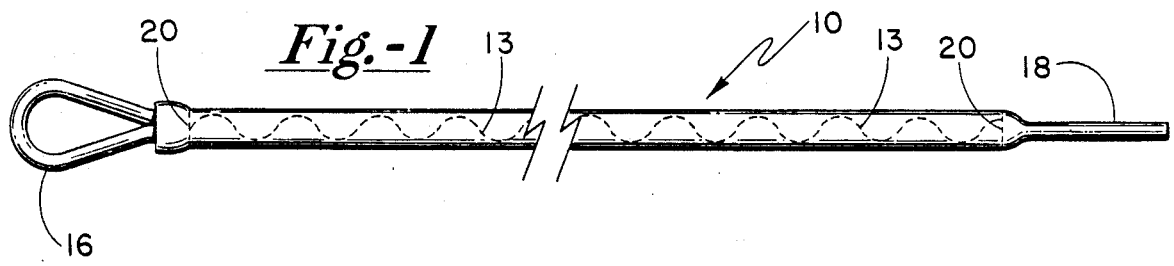
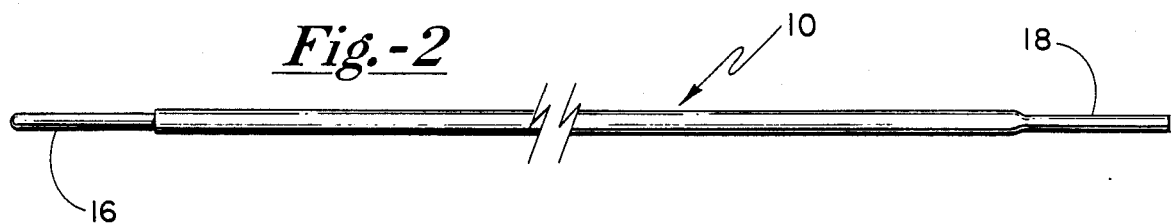
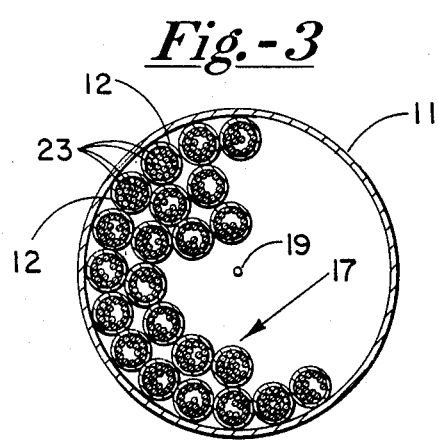
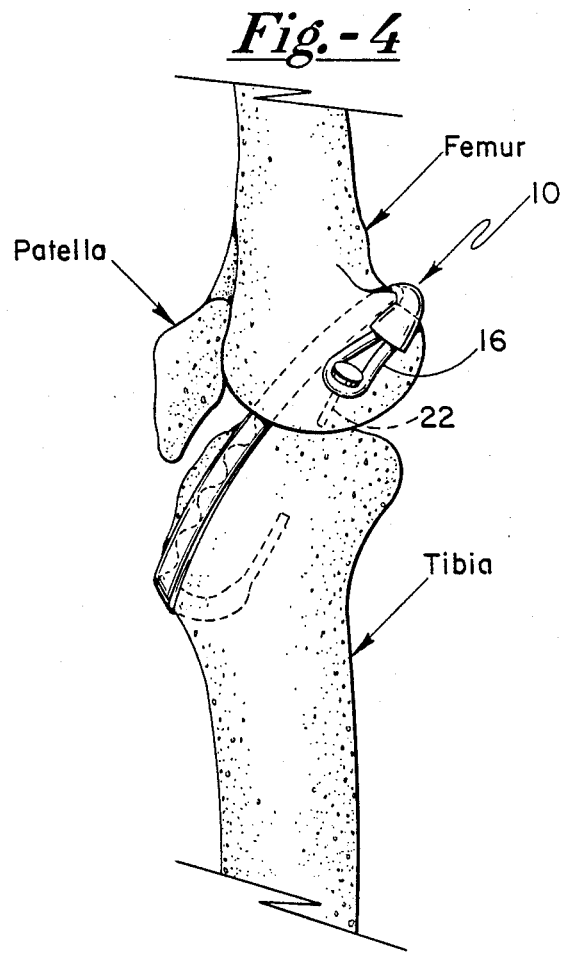

Stress-Strain Curve of Yarn

Stress-Strain Curve of Prosthetic

PROSTHETIC LIGAMENT

FIELD OF THE INVENTION

This invention is directed toward providing a prosthetic ligament utilizing synthetic materials.

DESCRIPTION OF THE PRIOR ART

Replacement of anatomical parts using prosthetic devices designed to carry out similar functions frequently becomes the solution of choice when other medical alternatives have been exhausted. Numerous prosthetic devices are available as replacements for almost all of the major anatomical functions. For example, orthopedic surgery for replacement of diseased hips and knees with prosthetic hip and knee joints has become quite common as effective devices have been developed. However, a similar trend has not been noted for ligaments, largely due to the fact that adequate prosthetic devices have not yet been developed.

A conventional medical intervention for the repair of damaged ligaments involves the surgical harvesting of tissue from one portion of the body to be used for ligament repair elsewhere. One example is the use of fascia lata (fascial strip) to repair damaged ligaments. This is not satisfactory since extensive surgery is involved, and the repair or replacement tissue does not always function adequately in situ.

The medical community has prescribed certain characteristics for prosthetic ligaments. While all the properties influencing the ultimate success of a ligament prosthesis have not yet been defined, the following are some of the most important desired characteristics:
1. Adequate strength;
2. Resistance to elongation;
3. Fixation methods, the device should be easy to implant and attach;
4. Biocompatability, as demonstrated by a minimum of inflammatory responses;
5. Longevity, the device should last the lifetime of the patient;
6. Tissue ingrowth, host tissue should be able to penetrate the device to stabilize and ultimately enhance the device's physical property;
7. Activity, the implanted device should allow early if not immediate use of the limb;
8. Pliability;
9. Resistance to abrasion.

Various attempts have been made to design devices that meet the aforementioned criteria. One such device, described in U.S. Pat. No. 4,483,023 by Hoffman, et al., comprises a knitted polyester sheath surrounding a core of polyester strands. One of the deficiencies of the Hoffman device is that the longevity of the device is likely to be severely limited by a slow degradation of the polyester materials used to construct the sheath of the device. Invivo experience utilizing similar polyester yarns for cardiovascular devices has indicated that substantial losses of strength may accompany the use of these lower tenacity polyester yarns in implanted devices. Further, tissue ingrowth is likely to be slowed by the knitted polyester sheath which ultimately slows the healing process.

The device constructed in accordance with the teachings of the Hoffman '023 patent contains a woven or braided core. While woven core yarns may possess adequate strength, they intrinsically are less pliable thus detracting from this important aspect of the device. Alternately, braiding of the core yarn which might improve the pliability of the device would lead to a construction intrinsically lower in tensile strength as well as a device that would be subject to early failure resulting from the cutting action of the braided core yarns upon themselves when they were subjected to stress loads.

U.S. Pat. No. 4,149,277 introduces another variant in the construction of prosthetic ligaments and tendons in the form of carbon coated polyester filaments in braided, woven or meshed array. Carbon has long been known to be effective in improving the biocompatability of biomedical devices. Carbon coated polymeric devices constructed in accordance with the teachings of the '277 patent would expectedly exhibit better biocompatability than most noncoated polymeric constructions. However, as a result of the contact of yarns in braided, woven, or meshed constructions ultimately a delamination of carbon from these points could occur, thus reducing the biocompatability of the device. In addition, the devices constructed in accordance with the teaching of the '277 patent would suffer from the same problems encountered in woven or braided constructions described in the '023 patent.

U.S. Pat. No. 4,585,458 describes the use of chemically fixed heterologous collagenous tissues instead of synthetic materials for repair or replacement of ligaments or tendons. At present such devices have not proven to be effective alternatives for ligament repair since they typically exhibit premature failure.

SUMMARY OF THE INVENTION

An improved ligament prosthesis exhibiting greater pliability and improved host tissue response is constructed with an outer sheath of braided yarns of polytetrafluoroethylene (PTFE), commonly known under the trademark TEFLON, and a lumen core composed of multiple high tenacity yarns or strands of synthetic materials such as polyester lying in linear array along or parallel to the longitudinal axis of the sheath. Multifilamentous PTFE and polyester yarns were first investigated for medical applications during the 1950's. Since that time experiments and experiences with these materials have established that they are suitable for biomedical applications and have most, if not all, of the desired characteristics when used in proper combination to produce prosthetic ligaments.

To insure an integral unit that will uniformly respond to stresses, the sheath and core are attached together by stitching the two components together using a polyester or PTFE multifilamentous yarn. To expedite healing, collagen materials as well as polylactic acid may be coated onto the core yarns as well as the sheath material. As a further feature, a loop may be provided for attaching the device to a bone at one end by placing an anchoring bone screw through the loop when the device is placed in situ.

Yet another feature of the invention is the inclusion of a radiopaque filament such as barium sulfate (Ba So4) filled polypropylene in the core to assist in x-ray viewing of the device after it has been implanted in situ.

By placing the core strands or yarn side-by-side linearally along or parallel to the longitudinal axis of the sheath, the strands are prevented from crossing over one another thereby eliminating or minimizing the possibility of abrasion which might otherwise weaken or tear the core strands after implant. Since the core yarns are not woven nor braided together, the device exhibits greater pliability and thus constitutes a major improvement in regard to surgical utility.

Stitching through the sheath and the core strands in a zig-zag or wavy pattern, or, alternatively with an evenly spaced cross (x) pattern, holds the two together so the device will operate in situ as an integral unit and there will be relatively little movement between the outer sheath and the core.

The sheath made of braided PTFE yarn is porous to provide a more satisfactory controlled ingrowth of host tissue to stabilize the device. The tissue ingrowth into the device constructed utilizing multifilamentous PTFE yarns exhibits a more uniform, less inflammatory tissue (host) response than that noted in polyester devices. Also, PTFE is highly resistant to degradation by chemical activity when in situ, it is highly inert, and because of its low coefficient of friction, is less susceptible to damage by abrasion.

A coating material such as polylactic acid or collagen facilitates the healing and further enhances the biocompatability of the device in situ while it may also act as a carrier for any medications such as antibiotics, which might be administered.

As a further feature, the device may be provided with a removable introducer tip for use in stringing the prosthetic ligament when being placed in situ. Alternatively, the ends may be potted or stiffened in a suitable material such as polyurethane or silicone for this same purpose.

DESCRIPTION OF THE DRAWING

FIG. 1 is what might be considered a side view of a preferred embodiment of a prosthetic device constructed according to the teachings of the invention with a zig-zag or wavy continuous stitching pattern;

FIG. 2 is correspondingly what might be considered a top or bottom view of the embodiment shown in FIG. 1;

FIG. 3 is a somewhat enlarged cross-section view showing the relationship of the core yarns to the sheath before stitching;

FIG. 4 is an illustration of an embodiment of the invention placed in situ;

DESCRIPTION OF THE PREFERRED EMBODIMENTS

Figure 5:
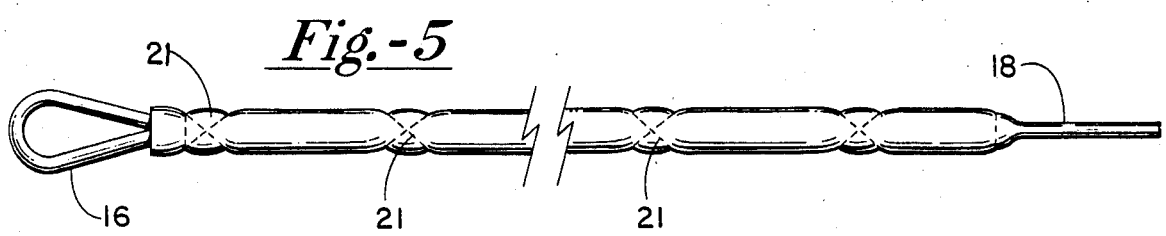
FIG. 5 illustrates an alternate stitching pattern.

The prosthetic device, designated generally by reference numeral 10, has an outer tubular sheath 11 surrounding a core 17 of elongated multifilamentous relatively high tenacity yarns or strands 12 of a synthetic material such as polyester. Each of the strands or yarns 12 is made up of a multitude of fibres or filaments 23. The individual core strands 12 are arranged to rest side by side linearally along and parallel to one another and parallel to the longitudinal axis of the sheath lumen. The fabric of sheath 11 is made of braided multifilamentous strands of PTFE as compared to prior art devices, such as in the Hoffman U.S. Pat. No. 4,483,023, in which the sheath fabric is made from knitted strands of polyester. As mentioned earlier, both fabrics have some degree of permeability which permits tissue ingrowth but it has been found that the that the fabric made from braided PTFE produces a more satisfactory controlled tissue ingrowth apparently due to a combination of the braiding and the characteristics of the PTFE. Also, knitted polyester fabric is likely to deteriorate more rapidly than knitted or braided PTFE when the ligament is placed in situ where it is subjected to the continuous motions and stresses encountered by the prosthetic ligament during normal use.

Core 17 is secured to sheath 11 by stitching 13 which passes through sheath 11 and core 17 in a zig-zag or wavy pattern along the entire length of the device. Stitching 13 randomly passes over, under and between different strands 12 in core 17 as it passes back and forth between sides of the sheath so that its overall effect, over the entire length of the device, is to firmly hold core strands 12 within sheath 11 so that the core and sheath generally act together as a single integral unit with a minimum amount of relative sliding motion between them. Preferably, stitching 13 is a single continuous zig-zag or wavy stitching extending over the entire length of the sheath, as illustrated in FIG. 1. Alternatively, the stitching may be a series of separate transverse or cross-stitches 21 spaced from one another along the entire length of the sheath as illustrated in FIG. 5, or may take other forms or patterns. The sheath may be closed off with a transverse stitch 20 near each end. One end of the device may be provided with a loop 16 which can be used to anchor one end of the prosthetic device when it is placed in situ. Loop 16 is formed merely by looping one end of the sheathed core back on itself and attaching the end, preferably by secure stitching, utilizing a polyester or PTFE thread.

Core 17 comprises in the range from about six to about seventy individual lengths or ends or strands of a relatively high tenacity polyester yarn such as, for example, 1100 denier, 192 filament Dacron T-73. Dacron T-73 has a tenacity of about nine grams per denier. Experience has shown that polyester having a tenacity greater than about five grams per denier is satisfactory. Preferably the packing density should be about sixty ends of yarn in a sheath having an outer diameter of about six mm. As an added feature, if it is desired to provide radiopacity, a radiopaque monofilament 19 may be included in the core. Typically a suitable monofilament of this nature will range from about five to fifteen mils in diameter and contain in the range from about 8% to about 20% barium sulfate (Ba So4) or other suitable material.

Typically, the fabric of sheath 11 is made from a suitable PTFE yarn, for example, a bleached 225 denier, 30 filament yarn utilizing about 40-70 picks per inch and has a water permeability ranging from about 20 to 200 ml/min/cm$^2$ when measured using a Wesolowski permeability tester @120 mm. Hg pressure as described in 4.3.1.2 of the American National standard (7-7-1986) for vascular prosthesis developed by A.A.M.I. The sheath fabric may be texturized, plyed or twisted to achieve surface characteristics more advantageous to tissue ingrowth. Because of the permeability, when the sheath is placed in situ host tissue ingrowth is facilitate to and through the sheath and to the core. Experience has shown that preferably the permeability should be in the range mentioned above but theoretically, there is no upper limit to the permeability provided the sheath can still perform its function of securely holding the core in place and withstand the forces normally encountered over extended periods of time after the prosthetic device is placed in situ. In one embodiment core 17 is integrally attached to sheath 11 by continuous zig-zag or wavy stitching 13 which preferably is in the range of about 6-15 stitches per inch along the long axis of the device through sheath 11 utilizing a multifilamentous synthetic thread such as PTFE or polyester. Initially, sheath 11 is cylindrical (see FIG. 3) but after the core has been inserted and zig-zag stitching 13 added, it takes on an elliptical shape. In this shape and form the device is flexible enough so that when being placed in situ, it can be inserted into and pass through any openings and can be turned and twisted as necessary without losing any of its characteristics as a suitable synthetic prosthetic ligament. Alternatively, sheath 11 may be attached to core 17 utilizing evenly spaced cross-stitches 21 as shown in FIG. 5. In this manner the cross section of the device will be elliptical or flattened at the stitches but will be generally circular between stitches, thus making it somewhat more flexible.

To assist in placing the device in situ, it may be provided with an introducer tip 18 at its distal end. Tip 18 is preferably a sleeve of heat shrinkable polyolefin material which is slipped over one end of the device and heated until it shrinks to firmly grasp onto the outer sheath. It can then be used as an aid by the operating physician to guide the prosthetic ligament into place and when the ligament is in place tip 18 is removed and discarded and then the end of the ligament is attached by the surgeon. Alternatively, an introducer tip may be provided at both ends.

As mentioned earlier, core strands 12 and sheath 11 may be coated to enhance stabilization of the implanted device by tissue ingrowth. Coating materials composed of insoluble, fibrillar collagen as well as soluble collagen may be used. As one example, an insoluble collagen coating matrix is prepared by adding two grams of collagen (for example a type sold under the brand name Secol LH4320) and five grams glycerol or sorbitol to 93 ml. H2O to form a 2% collagen slurry. The resulting slurry is heated $_{at}$ about 100° C. for a period of about twenty-five minutes to denature the collagen. When the slurry has cooled, it is introduced onto the core and mechanically massaged to insure complete coverage of the core yarns. Similarly, the PTFE sheath may be coated with the collagen slurry and is also mechanically massaged so that the slurry works its way into the interstices of the sheath in such a manner that the device is completely coated with collagen. The entire device is carefully placed into a 2% formalin bath for a period of about twenty-four hours to partially stabilize the collagen matrix. Alternately, the coated device may be placed on a manifold and vapor phase cross-linked using poly oxymethylene fumes for a period of several hours. Finally, the device is dried in a drying oven for about twenty-four hours at about 50° C. Subsequently the sheath and core are stitched together as described earlier. Other combinations of collagen, glycerol and H2O can be used and the same benefits derived.

Devices constructed in accordance with the teachings of this invention, with and without collagen coating, have been implanted subcutaneously in rats and qualitatively compared to polyester sheathed devices. After thirty days, the devices were explanted and histologically characterized. Tissue ingrowths were noted in both cases. The granular response around the PTFE sheath appeared extremely inert and did not exhibit the inflammatory responses typically noted for polyester sheathed prosthesis. The tissue ingrowth appeared to be more organized in the PTFE braided sheath with the sheath and core strands coated with collagen.

For reference, the packing density of the prosthetic ligament described herein can be generally considered to be the ratio of the number of core strands or yarns to the cross-sectional area of the sheath lumen prior to stitching. While to a degree the packing density may be a matter of choice, in general it is preferred that the packing density be such that the core strands or yarns substantially fill the area of the sheath lumen. Typically, for example, a Dupont Dacron T-73, 1100 denier, 192 filament occupies about 0.47 square mms. of cross-sectional area so if a sheath having a lumen diameter of approximately six mms. were utilized then the core should comprise about 60 ends. One of ordinary skill in the art can readily determine the packing density suitable for any size ligament knowing the size of the sheath and the core filaments. The packing density should be chosen such that the ligament has the required tensile strength for the specific application and that the stitching will cause the core to pack tightly so that the core filaments are held firmly in place and the core and sheath act as a single integral unit, minimizing the possibility of any sliding motion between the core filaments and the sheath.

FIG. 4 illustrates one manner in which an embodiment of the invention may be placed in situ. A pin 22 may be inserted into the femur to anchor loop 16 and the prosthetic ligament 10 is then wrapped part way around the lower end of the femur and between the femur and tibia and under the patella and attached to the tibia in some convenient fashion by the operating surgeon.

Figure 6:
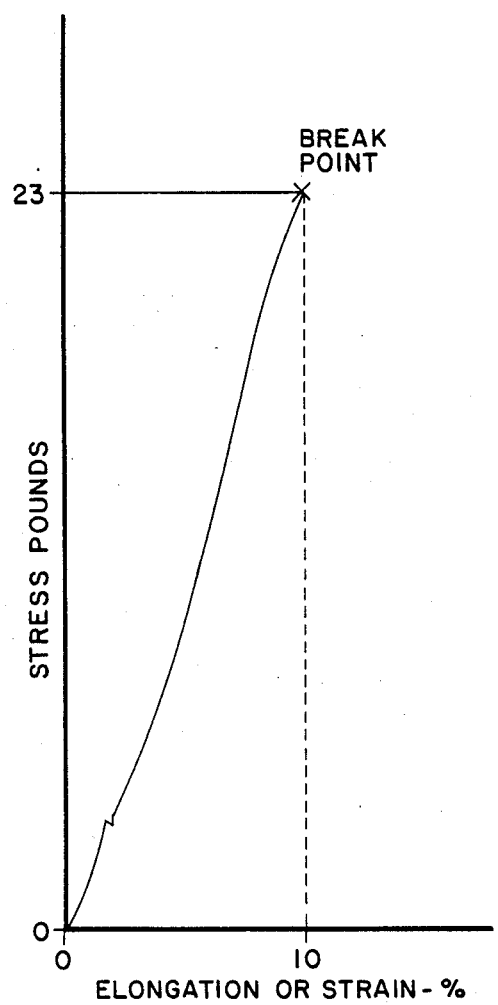
FIG. 6 is a graph illustrating the tensile strength of the core yarns used in an embodiment of the invention.

FIG. 6 is a reproduction of an actual stress-strain curve of T-73, 1100/192 Dupont polyester yarn used in the core of an embodiment constructed according to the teachings of this invention. It illustrates that the core yarn will elongate up to about 10% of its original length before it will break at an applied stress force of about 23 pounds.

Figure 7:
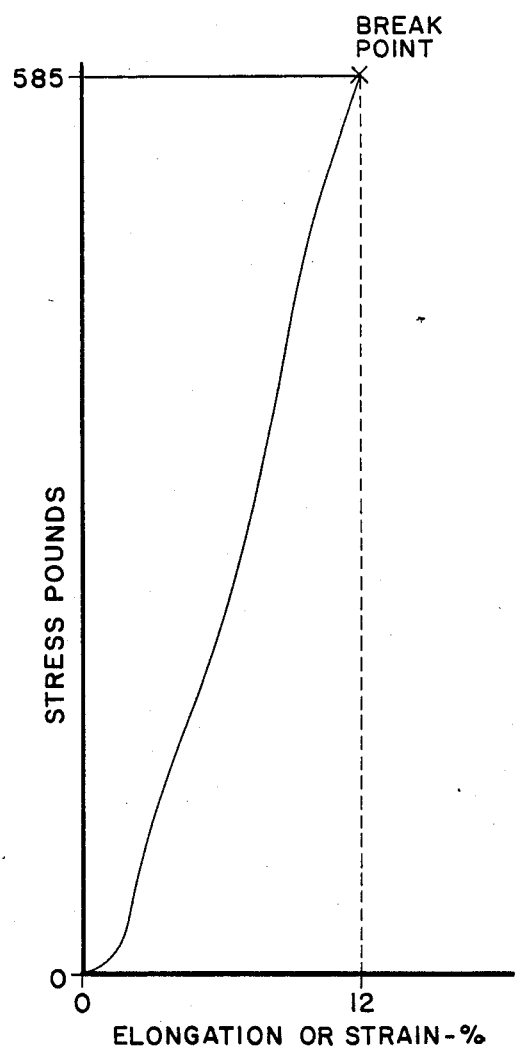
FIG. 7 is a graph illustrating the tensile strength of an embodiment of the invention.

FIG. 7 is a reproduction of an actual stress-strain curve of a prosthetic ligament constructed according to the teachings of this invention having a thirty end core of the yarn tested in FIG. 6. FIG. 7 illustrates that the ligament will elongate up to about 12% of its original length before it will break at an applied stress force of about 585 pounds.

We claim:

1. A ligament prosthesis for implanting in situ in a body, comprising:
    an elongated tubular porous sheath made of PTFE yarn;
    an unwoven non-braided core within said sheath, said core comprising a plurality of linearly arranged high tenacity strands of polyester running generally parallel to one another and to the central axis of said sheath;
    said core being anchored to said sheath with a stitching of multifilamentous synthetic thread passing through said sheath and said core.

2. The prosthetic ligament as in claim 1 wherein said sheath has a permeability sufficient to permit tissue ingrowth into the sheath when placed in situ.

3. The prosthetic ligament as in claim 1 wherein said sheath is characterized by having a permeability in the range of about 20 to 200 ml/min/cm$^2$ and a density of about 40-70 picks per inch.

4. The prosthetic ligament as in claim 1 wherein said stitching is a continuous zig-zag or wavy pattern along the length of the sheath and in the range of about six to fifteen stitches per inch.

5. The prosthetic ligament as in claim 4 wherein the sheath is generally elliptical in cross-section.

6. The prosthetic ligament as in claim 1 wherein said core comprises in the range from about six to about seventy strands.

7. The prosthetic ligament as in claim 6 wherein said strands each have a tenacity greater than about five grams per denier.

8. The prosthetic ligament as in claim 1 further including a radiopaque monofilament in said core.

9. The prosthetic ligament as in claim 1 further including a collagen coating on said core strands and on said sheath for inducing tissue growth.

10. The prosthetic ligament as in claim 1, said ligament having two ends and further including a guide tip attached to an end of said ligament.

11. The prosthetic ligament as in claim 1, said ligament having two ends and further including a loop at an end of said ligament formed by looping the end back onto the ligament and attaching it thereto.

12. The prosthetic ligament as in claim 1 wherein said sheath is made of bleached 225 denier 30 filament yarn of about 40–70 picks per inch.

13. The prosthetic ligament as in claim 1 wherein said core comprises in the range of about 6 to 70 strands of yarn each in the range of about 0.47 square mms. in cross-sectional area.

14. The prosthetic ligament as in claim 1 wherein said sheath yarns are braided.

15. The prosthetic ligament as in claim 1 wherein said sheath yarns are woven.

16. The prosthetic ligament as in claim 1 wherein said sheath yarns are knitted.

17. The prosthetic ligament as in claim 1 wherein said stitching comprises a series of separate cross-stitches spaced from one another along the length of the sheath.

* * * * *